(12) United States Patent
Saint Vrestil (10) Patent No.: US 11,790,712 B1
(45) Date of Patent: Oct. 17, 2023

(54) PRESCRIPTION DRUG DISPENSING DEVICE

(71) Applicant: James Saint Vrestil, Mableton, GA (US)

(72) Inventor: James Saint Vrestil, Mableton, GA (US)

( * ) Notice: Subject to any disclaimer, the term of this patent is extended or adjusted under 35 U.S.C. 154(b) by 0 days.

(21) Appl. No.: 17/742,495

(22) Filed: May 12, 2022

(51) Int. Cl.
| | |
|---|---|
| *G07C 9/00* | (2020.01) |
| *G16H 20/13* | (2018.01) |
| *A61J 1/03* | (2023.01) |
| *A61J 7/00* | (2006.01) |

(52) U.S. Cl.
CPC ............ *G07C 9/00563* (2013.01); *A61J 1/03* (2013.01); *A61J 7/0076* (2013.01); *G16H 20/13* (2018.01); *A61J 2200/70* (2013.01); *A61J 2205/60* (2013.01)

(58) Field of Classification Search
CPC ....... G07C 9/00563; A61J 1/03; A61J 7/0076; A61J 2200/70; A61J 2205/60; G16H 20/13
See application file for complete search history.

(56) References Cited

U.S. PATENT DOCUMENTS

| | | | | |
|---|---|---|---|---|
| 5,047,948 A | * | 9/1991 | Turner | ................... A61J 7/0436 221/9 |
| 6,004,020 A | * | 12/1999 | Bartur | ..................... G07F 9/002 700/242 |
| 7,978,564 B2 | * | 7/2011 | De La Huerga | .. A61M 5/16827 700/242 |
| 9,489,491 B2 | * | 11/2016 | Chrusciel | ............... G16H 20/13 |
| 9,597,262 B2 | | 3/2017 | Morgan | |
| D806,567 S | | 1/2018 | Ammar | |
| 9,974,713 B1 | * | 5/2018 | Song | ..................... A61J 7/0445 |
| 10,026,295 B2 | | 7/2018 | Johnson | |
| 10,872,482 B1 | | 12/2020 | Colton | |
| 10,945,925 B2 | | 3/2021 | Patel | |
| 11,135,131 B2 | | 10/2021 | Aliakbarian | |
| 2009/0223994 A1 | * | 9/2009 | Getz | .................. B65D 83/0427 221/154 |
| 2014/0214200 A1 | * | 7/2014 | Chrusciel | ............... A61J 7/0076 221/15 |
| 2014/0358278 A1 | * | 12/2014 | Zhang | .................... G16H 20/13 700/240 |
| 2015/0202588 A1 | * | 7/2015 | Allphin | ................ A61K 31/191 422/187 |

(Continued)

*Primary Examiner* — Michael Collins (57) ABSTRACT

A prescription drug dispensing device for controlled dosing of capsules, pills, and tablets includes an access control, dispensing, and communication module, which is integral to a container. The container comprises a body, for holding a prescription drug for a user, and a lid to secure the prescription drug in the container. The access control, dispensing, and communication module is programmable with a biometric characteristic of the user and a dosing regimen. The access control, dispensing, and communication module dispenses a dose of the prescription drug, according to the dosing regimen, and sends dosing data to one or both of a smartphone of a user and an electronic device of a prescriber or a pharmacist. A tamper sensor detects an unauthorized attempt to open the container and sends a tampering signal to a dispenser, which dispenses a chemical solution onto the prescription drug to render the prescription drug inactive.

7 Claims, 4 Drawing Sheets

(56) References Cited

U.S. PATENT DOCUMENTS

| | | |
|---|---|---|
| 2017/0281467 A1 | 10/2017 | Solotoff |
| 2018/0308327 A1* | 10/2018 | Dobbins ............ G08B 13/1427 |
| 2020/0206084 A1* | 7/2020 | Tsukanov .................. A61J 1/03 |
| 2021/0043295 A1* | 2/2021 | Macoviak ............ A61B 5/7275 |
| 2021/0264716 A1* | 8/2021 | Norbeck ................. G07F 11/58 |

* cited by examiner

PRESCRIPTION DRUG DISPENSING DEVICE

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to dispensing devices and more particularly pertains to a new dispensing device for controlled dosing of capsules, pills, and tablets. The present invention discloses a dispensing device comprising a container with an integral access control, dispensing, and communication module, which is programmable with a biometric characteristic of the user and a dosing regimen and which sends dosing data to one or both of a smartphone of a user and an electronic device of a prescriber or a pharmacist. The present invention also includes a tamper sensor and a chemical solution to render the prescription drug inactive if unauthorized access is attempted.

(2) Description of Related Art Including Information Disclosed Under 37 CFR 1.97 and 1.98

The prior art relates to dispensing devices. Prior art dispensing devices may comprise prescription bottles with notification capabilities, one or both of visual and audible, prescription bottles with timed dispensing capabilities, prescription bottles with usage monitors and communication capabilities, prescription bottles with biometric scanners for allowing lid opening, and double walled prescription bottles having an aversive fluid positioned between that walls that is released upon detection of unauthorized access. What is lacking in the prior art is a dispensing device comprising a container with an integral access control, dispensing, and communication module, which is programmable with a biometric characteristic of the user and a dosing regimen, and which sends dosing data to one or both of a smartphone of a user and an electronic device of a prescriber or a pharmacist. Additionally lacking in the prior art is such a dispensing device comprising a tamper sensor, which detects an unauthorized attempt to open the container and sends a tampering signal to a dispenser, which dispenses a chemical solution onto the prescription drug to render the prescription drug inactive.

BRIEF SUMMARY OF THE INVENTION

An embodiment of the disclosure meets the needs presented above by generally comprising a container, which comprises a body and a lid. The body is configured to be loaded with a prescription drug for a user. The lid is lockable to the body to secure the prescription drug in the container. An access control, dispensing, and communication module is integral to the container and is selectively programmable with a biometric characteristic of the user and a dosing regimen for the prescription drug. The access control, dispensing, and communication module is configured to dispense a dose of the prescription drug, according to the dosing regimen, and to communicate dosing data to one or both of a smartphone of a user and an electronic device of a prescriber or a pharmacist. A tamper sensor is engaged to the container and is configured to detect an unauthorized attempt to open the container and to generate a tampering signal. A dispenser engaged to the container and operationally engaged to the tamper sensor is positioned to dispense a chemical solution onto the prescription drug upon receipt of the tampering signal from the tamper sensor. The chemical solution is configured to render the prescription drug inactive.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

With reference now to the drawings, and in particular to FIGS. 1 through 5 thereof, a new dispensing device embodying the principles and concepts of an embodiment of the disclosure and generally designated by the reference numeral 10 will be described.

As best illustrated in FIGS. 1 through 5, the prescription drug dispensing device generally comprises a container 12, which in turn comprises a body 14 and a lid 16. The body 14 is configured to be loaded with a prescription drug 18, such as a controlled substance, for a user. The container 12 may comprise metal, or other substantially impenetrable material, such as, but not limited to, containment grade plastic, ballistic grade plastic, and the like.

The lid 16 is lockable to the body 14 to secure the prescription drug 18 in the container 12. The lid 16 may be threadedly couplable to the body 14, although the present invention also anticipates the lid 16 being attachable and lockable to the body 14 by a variety of methods known to those skilled in the art of tamper resistant containers, such as, but not limited to, hinged caps, insertable caps, and the like, in combination with electronically actuated locks.

Figure 1:
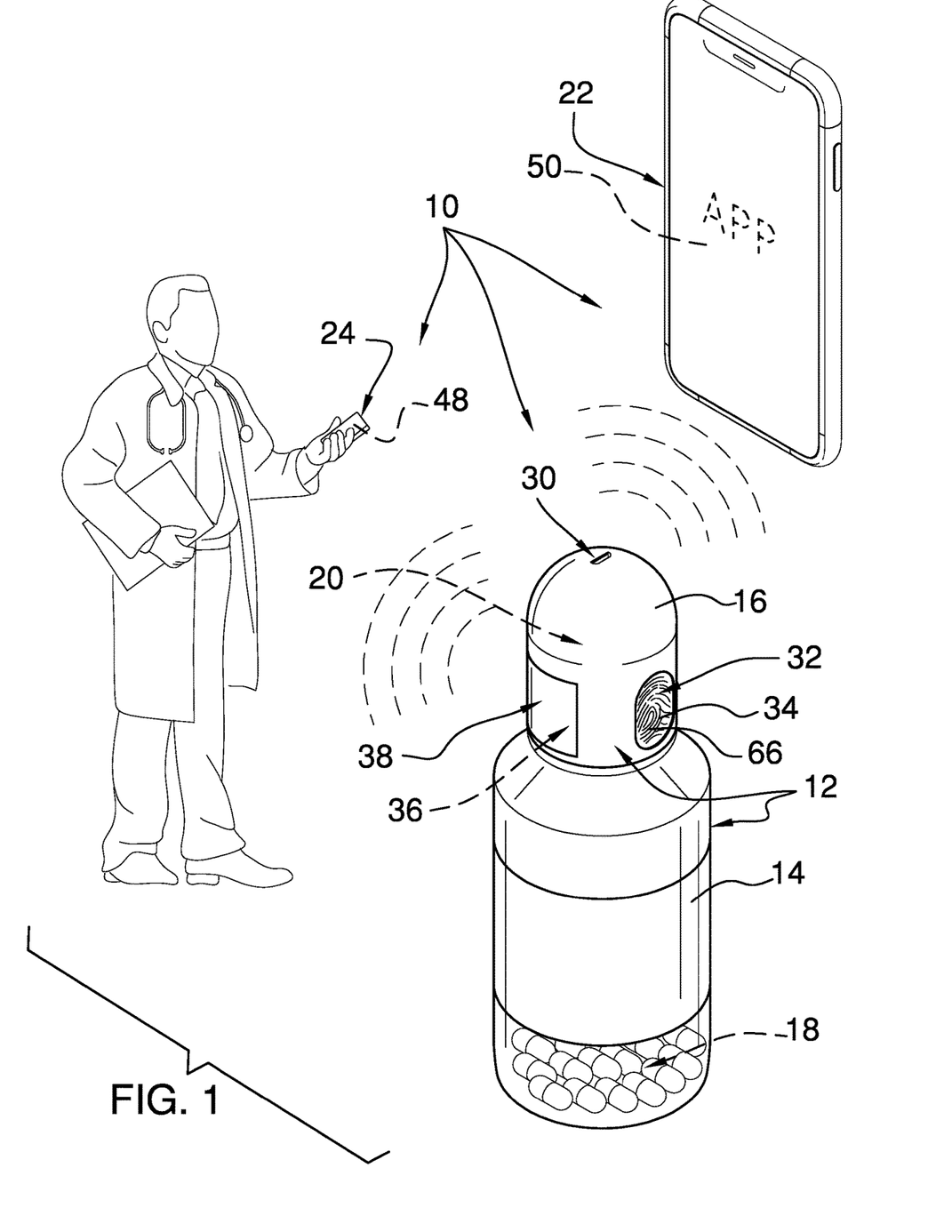
FIG. 1 is an in-use view of a prescription drug dispensing device according to an embodiment of the disclosure.
Figure 2:
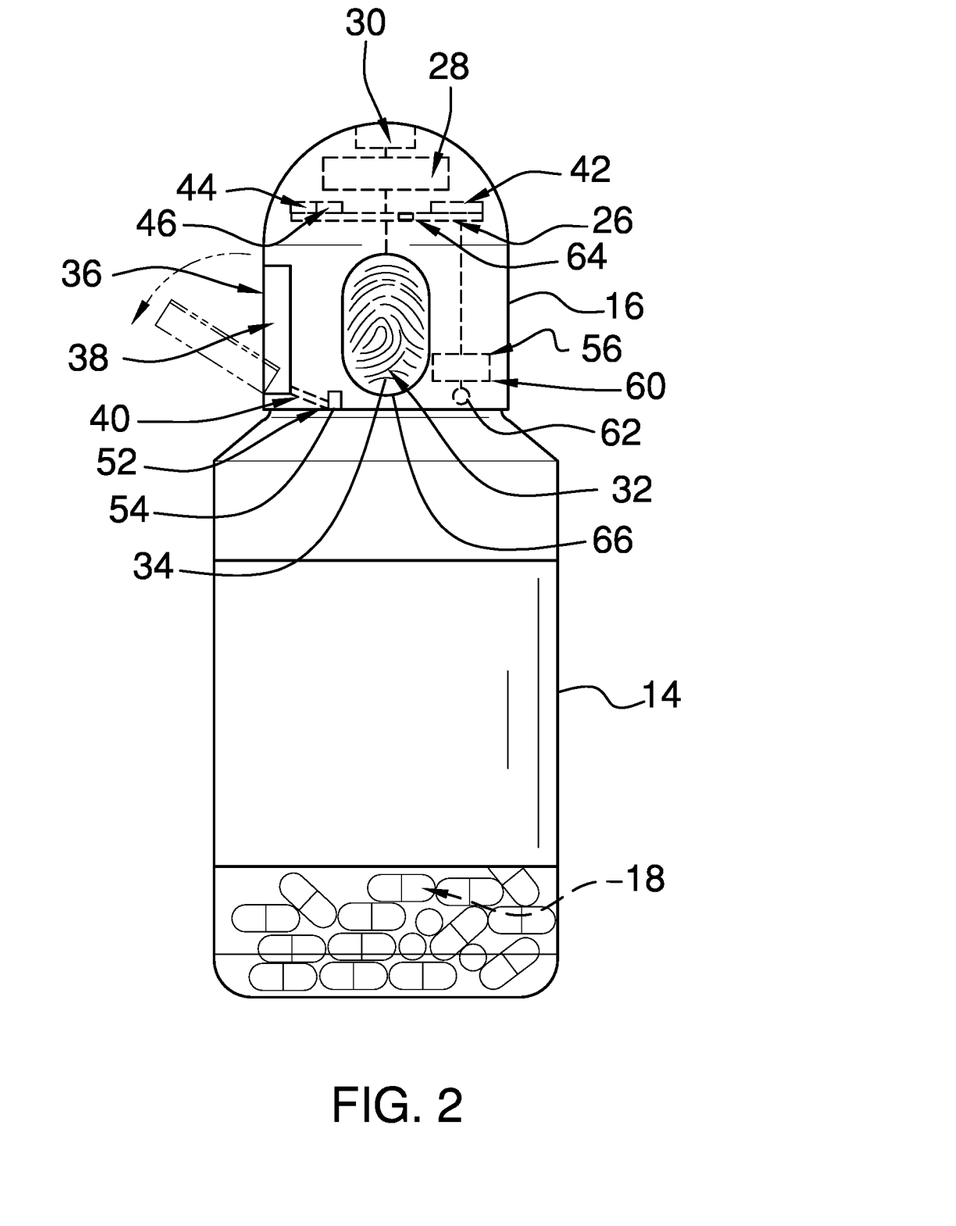
FIG. 2 is a side view of an embodiment of the disclosure.
Figure 3:
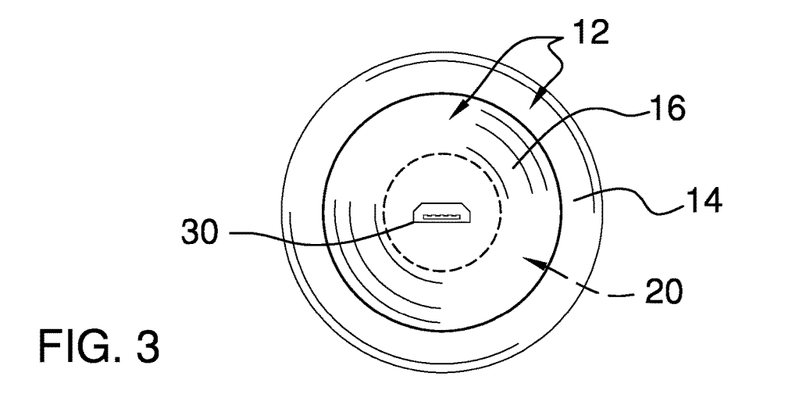
FIG. 3 is a top view of an embodiment of the disclosure.
Figure 4:
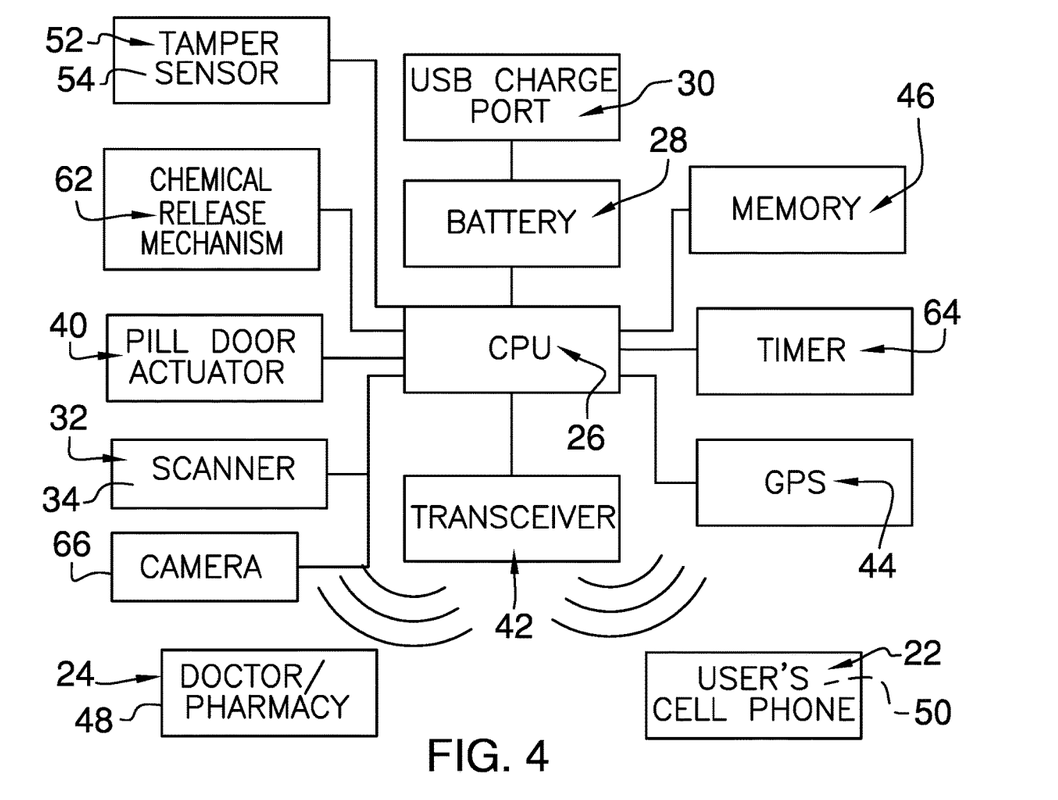
FIG. 4 is a block diagram of an embodiment of the disclosure.
Figure 5:
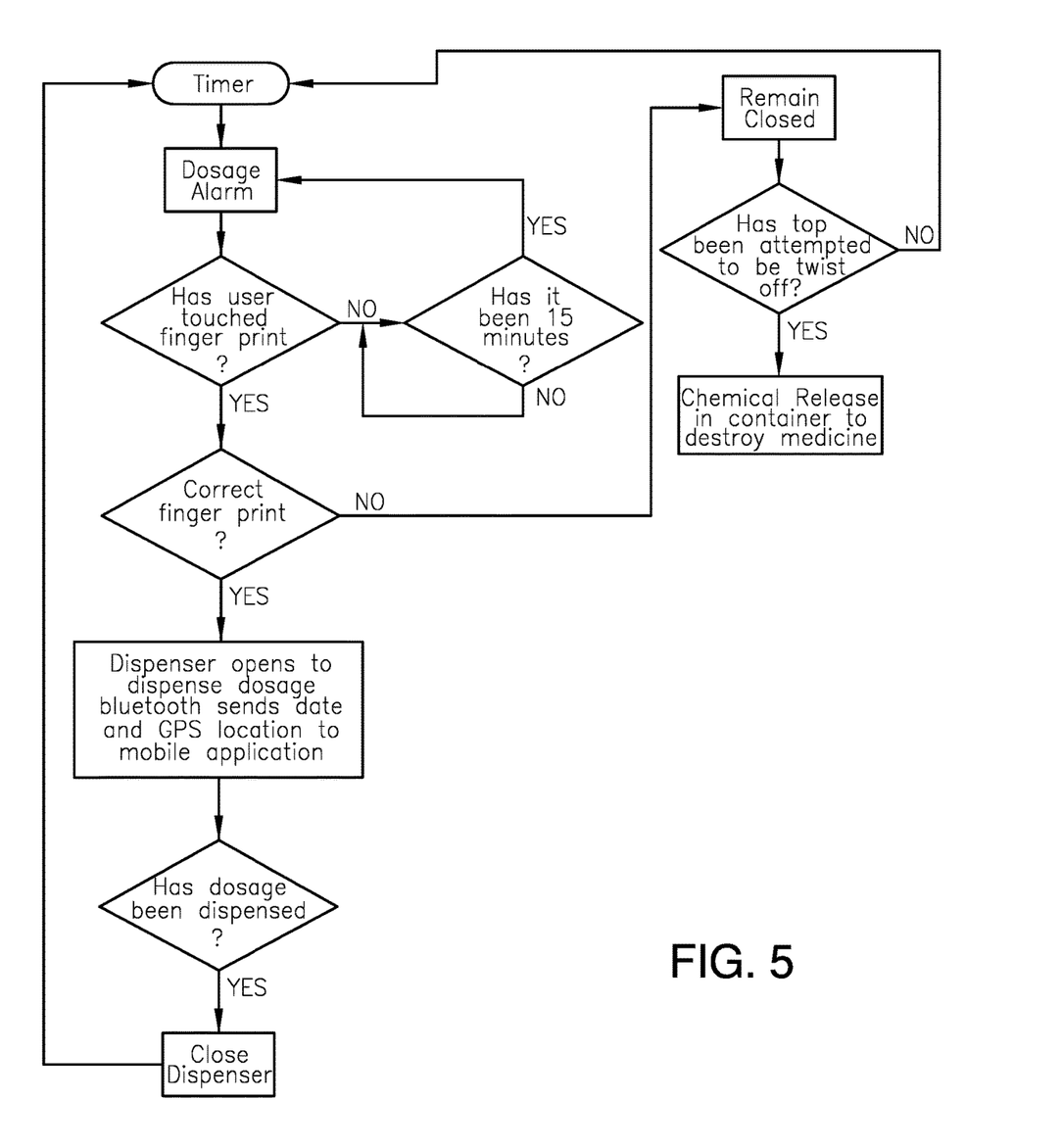
FIG. 5 is a flow diagram of an embodiment of the disclosure.

An access control, dispensing, and communication module 20 is integral to the container 12 and is selectively programmable with a biometric characteristic of the user and a dosing regimen for the prescription drug 18. The access control, dispensing, and communication module 20 is configured to dispense a dose of the prescription drug 18, according to the dosing regimen, and to communicate dosing data to one or both of a smartphone 22 of the user and an electronic device 24 of a prescriber or a pharmacist. As shown in FIG. 2, the access control, dispensing, and communication module 20 is integral to the lid 16, although the present invention also anticipates the access control, dispensing, and communication module 20 being integral to the body 14.

The access control, dispensing, and communication module 20 comprises a microprocessor 26, which in turn comprises an integral timer 64. A battery 28, which is rechargeable, is operationally engaged to the microprocessor 26. A port 30 is operationally engaged to the battery 28 and is configured to engage a plug of a charging cord (not shown) to connect the battery 28 to a source of electrical current to charge the battery 28.

A biometric scanner 32 is operationally engaged to the microprocessor 26 and is configured to scan the biometric characteristic of the user and to communicate a scan to the microprocessor 26 for verification. The biometric scanner 32 may comprise one or both of a fingerprint scanner 34, as shown in FIG. 2, and a camera 66, which is configured for facial recognition, or other biometric scanning means, such as, but not limited to, voice scanner, iris scanner, and the like.

An opening 36 is positioned in the container 12 and is selectively closable by a door 38, which is hingedly attached to the container 12. An actuator 40 is operationally engaged to the door 38 and the microprocessor 26, enabling the microprocessor 26 to signal the actuator 40 to open the door 38 upon verification of the scan, and when in compliance with the dosing regimen, so that a dose of the prescription drug 18 is dispensable through the opening 36 for the user.

A first transceiver 42 and a second transceiver 44 are operationally engaged to the microprocessor 26. The second transceiver 44 is Global Positioning System enabled and thus is configured to receive position coordinates corresponding to a location of the container 12. The first transceiver 42 selectively transmits dosing data and the position coordinates.

The access control, dispensing, and communication module 20 also may comprise a data storage module 46, which is operationally engaged to the microprocessor 26. The data storage module 46 enables the prescription drug dispensing device 10 to store the dosing data and the position coordinates.

Operator programming code 48, which is selectively positionable on the electronic device 24 of a prescriber or a pharmacist, enables the electronic device 24 to program the access control, dispensing, and communication module 20 with the biometric characteristic of the user and the dosing regimen for the prescription drug 18. The operator programming code 48 also enables the electronic device 24 to receive the dosing data and the position coordinates from the first transceiver 42 and to store the dosing data and the position coordinates on the electronic device 24.

User programming code 50, which is selectively positionable on a smartphone 22 of the user, enables the smartphone 22 to activate one or more of an audible notification and a visual notification upon receipt of a signal from the first transceiver 42 of a dosing event. These notifications serve to remind the user that it is time to take a dose of the prescription drug 18. The user programming code 50 also enables the smartphone 22 to receive the dosing data and the position coordinates from the first transceiver 42 and to store the dosing data and the position coordinates on the smartphone 22. Having access to the position coordinates allows locating of the container 12 in the event it is lost or stolen.

A tamper sensor 52 is engaged to the container 12 and is operationally engaged to the microprocessor 26. The tamper sensor 52 is configured to detect an unauthorized attempt to open the container 12 and to generate a tampering signal. The tamper sensor 52 may comprise an ambient light sensor 54, or other tampering detection means, such as, but not limited to, Hall-effect sensors, inductive sensors, and the like. When comprising an ambient light sensor 54, the tamper sensor 52 would be deactivated with successful verification of the scan from the biometric scanner 32. A dispenser 56 is engaged to the container 12 and is operationally engaged to the tamper sensor 52. The dispenser 56 is positioned to dispense a chemical solution 58, such as, but not limited to, an acidic solution, a basic solution, or the like, onto the prescription drug 18 upon receipt of the tampering signal from the tamper sensor 52. The chemical solution 58 is configured to render the prescription drug 18 inactive.

As shown in FIG. 2, the dispenser 56 comprises a void 60, which is positioned in the lid 16. The void 60 is in fluidic communication with the body 14 by means of a valve 62, which is operationally engaged to the microprocessor 26. The microprocessor 26 actuates the valve 62 upon receipt of a tampering signal, allowing the chemical solution 58 to flow into the body 14 of the container 12 to inactivate the prescription drug 18. The present invention also anticipates the dispenser 56 comprising reservoirs in combination with pumps, plungers, and the like.

In use, a prescriber or a pharmacist loads a prescription drug 18 into the body 14 and attaches the lid 16 to the body 14. The prescriber or pharmacist then programs the access control, dispensing, and communication module 20 with a biometric characteristic of a user and a dosing regimen for the prescription drug 18. The user then can access a dose of the prescription drug 18 at selected intervals, in compliance with the dosing regimen, by placing their finger upon the fingerprint scanner 34 or their face in front of the camera 66. Should the user, or another party, attempt to access the prescription drug 18 by tampering with the container 12, the chemical solution 58 will flow into the body 14 of the container 12 to inactivate the prescription drug 18.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A prescription drug dispensing device comprising:
a container comprising a body and a lid, wherein the body is configured for being loaded with a prescription drug for a user, the lid being lockable to the body for securing the prescription drug in the container, wherein the lid is threadedly couplable to the body;
an access control, dispensing, and communication module integral to the container, the access control, dispensing, and communication module being selectively programmable with a biometric characteristic of the user and a dosing regimen for the prescription drug, configured for dispensing a dose of the prescription drug according to the dosing regimen, and configured for communicating dosing data to one or both of a smartphone of a user and an electronic device of a prescriber or a pharmacist;
a tamper sensor engaged to the container and configured for detecting an unauthorized attempt to open the container and for generating a tampering signal, wherein the tamper sensor comprises an ambient light sensor;
a dispenser engaged to the container and operationally engaged to the tamper sensor being positioned for dispensing a chemical solution onto the prescription drug upon receipt of the tampering signal from the tamper sensor, wherein the chemical solution is configured for rendering the prescription drug inactive;
wherein the access control, dispensing, and communication module is integral to the lid, wherein the access control, dispensing, and communication module comprises:
a microprocessor comprising an integral timer, the tamper sensor being operationally engaged to the microprocessor;
a biometric scanner operationally engaged to the microprocessor, wherein the biometric scanner is configured for scanning the biometric characteristic of the user and communicating a scan to the microprocessor for verification;
an opening positioned in the container;
a door hingedly attached to the container for selectively closing the opening;
an actuator operationally engaged to the door and the microprocessor, such that the microprocessor signals the actuator for opening the door upon verification of the scan when in compliance with the dosing regimen, such that a dose of the prescription drug is dispensable through the opening for the user;
a first transceiver operationally engaged to the microprocessor, such that dosing data are selectively transmissible via the first transceiver;
a battery operationally engaged to the microprocessor; and
a second transceiver operationally engaged to the microprocessor, the second transceiver being Global Positioning System enabled, wherein the second transceiver is configured for receiving position coordinates corresponding to a location of the container, such that the position coordinates are transmissible via the first transceiver;
user programming code selectively positionable on a smartphone of the user enabling the smartphone for:
activating one or more of an audible notification and a visual notification upon receipt of a signal from the first transceiver of a dosing event; and
receiving the dosing data and the position coordinates from the first transceiver and storing the dosing data and the position coordinates on the smartphone; and
operator programming code selectively positionable on an electronic device of a prescriber or a pharmacist enabling the electronic device for:
programming the access control, dispensing and communication module with the biometric characteristic of the user and the dosing regimen for the prescription drug; and
receiving the dosing data and the position coordinates from the first transceiver and storing the dosing data and the position coordinates on the electronic device.

2. The prescription drug dispensing device of claim 1, wherein the container comprises metal.

3. The prescription drug dispensing device of claim 1, wherein the biometric scanner comprises one or both of a fingerprint scanner and a camera configured for facial recognition.

4. The prescription drug dispensing device of claim 1, further including the access control, dispensing, and communication module comprising a data storage module operationally engaged to the microprocessor, such that dosing data and the position coordinates are storable upon the data storage module.

5. The prescription drug dispensing device of claim further including:
the battery being rechargeable; and
a port operationally engaged to the battery, wherein the port is configured tor engaging a plug of a charging cord for connecting the battery to a source of electrical current for charging the battery.

6. A prescription drug dispensing system comprising:
a container comprising a body and a lid;
a prescription drug for a user positioned in the body, the lid being lockable to the body for securing the prescription drug in the container;
an access control, dispensing, and communication module integral to the container, the access control, dispensing, and communication module being selectively programmable with a biometric characteristic of the user and a dosing regimen for the prescription drug, configured for dispensing a dose of the prescription drug according to the dosing regimen, and configured for communicating dosing data to one or both of a smartphone of a user and an electronic device of a prescriber or a pharmacist;

a tamper sensor engaged to the container and configured for detecting an unauthorized attempt to open the container and for generating a tampering signal;
a dispenser engaged to the container and operationally engaged to the tamper sensor, the dispenser being positioned for dispensing a chemical solution onto the prescription drug upon receipt of the tampering signal from the tamper sensor, such that the prescription drug is rendered inactive;
the access control, dispensing, and communication module comprising:
  a microprocessor comprising an integral timer, the tamper sensor being operationally engaged to the microprocessor,
  a biometric scanner operationally engaged to the microprocessor, wherein the biometric scanner is configured for scanning the biometric characteristic of the user and communicating a scan to the microprocessor for verification,
  an opening positioned in the container,
  a door hingedly attached to the container for selectively closing the opening,
  an actuator operationally engaged to the door and the microprocessor, such that the microprocessor signals the actuator for opening the door upon verification of the scan when in compliance with the dosing regimen, such that a dose of the prescription drug is dispensable through the opening for the user,
  a first transceiver operationally engaged to the microprocessor, such that dosing data are selectively transmissible via the first transceiver,
  a second transceiver operationally engaged to the microprocessor, the second transceiver being Global Positioning System enabled, wherein the second transceiver is configured for receiving position coordinates corresponding to a location of the container, such that the position coordinates are transmissible via the first transceiver,
  a data storage module operationally engaged to the microprocessor, such that dosing data and the position coordinates are storable upon the data storage module, and
  a battery operationally engaged to the microprocessor;
an electronic device in possession of a prescriber or a pharmacist;
operator programming code positioned on the electronic device enabling the electronic device for:
  programming the access control, dispensing, and communication module with the biometric characteristic of the user and the dosing regimen for the prescription drug, and
  receiving the dosing data and the position coordinates from the first transceiver and storing the dosing data and the position coordinates on the electronic device;
a smartphone in possession of the user; and
user programming code positioned on the smartphone enabling the smartphone for:
  activating one or more of an audible notification and a visual notification upon receipt of a signal from the first transceiver of a dosing event, and
  receiving the dosing data and the position coordinates from the first transceiver and storing the dosing data and the position coordinates on the smartphone.

7. A prescription drug dispensing device comprising:
a container comprising a body and a lid, wherein the body is configured for being loaded with a prescription drug for a user, the lid being lockable to the body for securing the prescription drug in the container, the container comprising metal, the lid being threadedly couplable to the body;
an access control, dispensing, and communication module integral to the container, the access control, dispensing, and communication module being selectively programmable with a biometric characteristic of the user and a dosing regimen for the prescription drug, configured for dispensing a dose of the prescription drug according to the dosing regimen, and configured for communicating dosing data to one or both of a smartphone of a user and an electronic device of a prescriber or a pharmacist, the access control, dispensing, and communication module being integral to the lid, the access control, dispensing, and communication module comprising:
  a microprocessor comprising an integral timer,
  a biometric scanner operationally engaged to the microprocessor, wherein the biometric scanner is configured for scanning the biometric characteristic of the user and communicating a scan to the microprocessor for verification, the biometric scanner comprising one or both of a fingerprint scanner and a camera configured for facial recognition
  an opening positioned in the container,
  a door hingedly attached to the container for selectively closing the opening,
  an actuator operationally engaged to the door and the microprocessor, such that the microprocessor signals the actuator for opening the door upon verification of the scan when in compliance with the dosing regimen, such that a dose of the prescription drug is dispensable through the opening for the user,
  a first transceiver operationally engaged to the microprocessor, such that dosing data are selectively transmissible via the first transceiver,
  a second transceiver operationally engaged to the microprocessor, the second transceiver being Global Positioning System enabled, wherein the second transceiver is configured for receiving position coordinates corresponding to a location of the container, such that the position coordinates are transmissible via the first transceiver, and
  a data storage module operationally engaged to the microprocessor, such that dosing data and the position coordinates are storable upon the data storage module;
a battery operationally engaged to the microprocessor, the battery being rechargeable,
a port operationally engaged to the battery, wherein the port is configured for engaging a plug of a charging cord for connecting the battery to a source of electrical current tier charging the battery;
a tamper sensor engaged to the container and configured for detecting an unauthorized attempt to open the container and for generating a tampering signal, the tamper sensor being operationally engaged to the microprocessor, the tamper sensor comprising an ambient light sensor;
a dispenser engaged to the container and operationally engaged to the tamper sensor, the dispenser being positioned for dispensing a chemical solution onto the prescription drug upon receipt of the tampering signal from the tamper sensor, wherein the chemical solution is configured for rendering the prescription drug inactive;

user programming code selectively positionable on a smartphone of the user enabling the smartphone for:
  activating one or more of an audible notification and a visual notification upon receipt of a signal from the first transceiver of a dosing event,
  receiving the dosing data and the position coordinates from the first transceiver and storing the dosing data and the position coordinates on the smartphone; and
operator programming code selectively positionable on an electronic device of a prescriber or a pharmacist enabling the electronic device for:
  programming the access control, dispensing, and communication module with the biometric characteristic of the user and the dosing regimen for the prescription drug, and
  receiving the dosing data and the position coordinates from the first transceiver and storing the dosing data and the position coordinates on the electronic device.

* * * * *